United States Patent
Masson et al.

(10) Patent No.: US 9,381,005 B2
(45) Date of Patent: Jul. 5, 2016

(54) SPRAY HEAD FOR TWO COMPONENT MIXER

(71) Applicants: Baxter International Inc., Deerfield, IL (US); Baxter Healthcare S.A., Glattpark (Opfikon) (CH)

(72) Inventors: Florent Masson, Brussels (BE); Thomas Deleurme, Nivelles (BE); Johanny Stanus, Gibecq (BE); Christophe Vermeiren, Jette (BE)

(73) Assignees: BAXTER INTERNATIONAL INC., Deerfield, IL (US); BAXTER HEALTHCARE S.A., Glattpark (Opfikon) (CH)

( * ) Notice: Subject to any disclaimer, the term of this patent is extended or adjusted under 35 U.S.C. 154(b) by 640 days.

(21) Appl. No.: 13/662,050

(22) Filed: Oct. 26, 2012

(65) Prior Publication Data
US 2014/0117116 A1  May 1, 2014

(51) Int. Cl.
*B05B 7/26* (2006.01)
*A61B 17/00* (2006.01)
(Continued)

(52) U.S. Cl.
CPC ....... *A61B 17/00491* (2013.01); *B01F 13/0023* (2013.01); *B01F 13/0027* (2013.01);
(Continued)

(58) Field of Classification Search
CPC ................ A61B 2017/00495; B01F 12/0087
USPC .............. 239/310, 304, 321, 329, 418, 416.5, 239/427, 463, 466, 461, 399, 303, 39, 8; 604/82, 83; 222/145.5, 137
See application file for complete search history.

(56) References Cited

U.S. PATENT DOCUMENTS

| | | | | |
|---|---|---|---|---|
| 4,316,673 A | * | 2/1982 | Speer | B01F 5/0609 366/337 |
| 4,505,157 A | * | 3/1985 | Hong Le | F16L 37/113 600/488 |

(Continued)

FOREIGN PATENT DOCUMENTS

| WO | WO9639212 | 12/1996 |
|---|---|---|
| WO | 03022457 | 3/2003 |

(Continued)

OTHER PUBLICATIONS

International Search Report, Jan. 24, 2014.

*Primary Examiner* — Arthur O Hall
*Assistant Examiner* — Viet Le
(74) *Attorney, Agent, or Firm* — Greer, Burns & Crain, Ltd.

(57) ABSTRACT

A device for mixing at least two separate streams of components which, when mixed, form a combined fluid stream. The device comprises a conduit with at least two separate passageways leading to exit openings at an end face of the conduit. Each passageway communicates with a separate component stream and is arranged to direct the separate component stream in a downstream direction. The exit openings each have a predetermined cross-sectional flow area. A separate channel is located at a downstream end of each passageway exit opening. The channels are arranged to redirect the flow from each passageway to an axial direction. A single mixing chamber communicates with all of the separate channels, the mixing chamber being arranged to receive each of the component streams at an upstream end thereof and to permit a mixing of the component streams. An outlet is arranged downstream of the mixing chamber through which the combined fluid stream is dispensed.

13 Claims, 6 Drawing Sheets

(51) Int. Cl.
*B01F 13/00* (2006.01)
*B01F 15/00* (2006.01)
*B05B 7/04* (2006.01)

(52) U.S. Cl.
CPC ... *B01F15/0087* (2013.01); *A61B 2017/00495* (2013.01); *A61B 2017/00522* (2013.01); *B05B 7/0408* (2013.01)

(56) References Cited

U.S. PATENT DOCUMENTS

| | | | |
|---|---|---|---|
| 4,631,055 A | 12/1986 | Redl et al. | |
| 4,846,405 A | 7/1989 | Zimmermann | |
| 5,116,315 A | 5/1992 | Capozzi et al. | |
| 5,582,596 A | 12/1996 | Fukunaga et al. | |
| 5,605,255 A * | 2/1997 | Reidel | A61B 17/00491 222/137 |
| 5,665,067 A | 9/1997 | Linder et al. | |
| 5,989,215 A | 11/1999 | Delmotte et al. | |
| 6,461,361 B1 | 10/2002 | Epstein | |
| 6,585,696 B2 | 7/2003 | Petersen et al. | |
| 6,620,125 B1 | 9/2003 | Redl | |
| 6,802,822 B1 | 10/2004 | Dodge | |
| 2003/0050597 A1 | 3/2003 | Dodge et al. | |
| 2009/0038701 A1 | 2/2009 | Delmotte | |
| 2010/0114158 A1 | 5/2010 | Hattan et al. | |
| 2010/0274279 A1 | 10/2010 | Delmotte | |

FOREIGN PATENT DOCUMENTS

| | | |
|---|---|---|
| WO | 2007084919 | 7/2007 |
| WO | 2010042341 | 4/2010 |

* cited by examiner

SPRAY HEAD FOR TWO COMPONENT MIXER

BACKGROUND

The present invention generally relates to a spray head for an inline mixer for mixing multiple components of a combined fluid stream.

Inline mixing of combined fluid streams, including fluid streams of different viscosities, may be useful in a wide variety of settings including the medical field. In one example of an application in the medical field, inline mixing of two or more combined fluid streams is employed to form a sealant, such as a tissue sealant, that is applied to human and animal tissue. Such sealant may be employed to seal or repair tissue at a surgical or wound site, to stop bleeding, seal wounds, treat burns or skin grafts and a variety of other purposes.

In the medical field, and more particularly in the field of tissue sealants used to seal or repair biological tissue, such sealant is typically formed from two or more components that, when mixed, form a sealant having sufficient adhesion for a desired application, such as to seal or repair skin or other tissue. Such sealant components are preferably biocompatible, and can be absorbed by the body, or are otherwise harmless to the body, so that they do not require later removal. For example, fibrin is a well known tissue sealant that is made from a combination of at least two primary components—fibrinogen and thrombin, which have, depending on the temperature, different viscosities of about 300 cps and 15 cps, respectively. Upon coming into contact with each other, the fibrinogen and thrombin components interact to form a tissue sealant, fibrin, which is extremely viscous.

Sealant components may be kept in separate containers and are combined prior to application. However, because sealant components such as fibrinogen and thrombin have different viscosities, complete and thorough mixing is often difficult to achieve. If the components are inadequately mixed, then the efficacy of the sealant to seal or bind tissue at the working surface is compromised.

To overcome the difficulties of the formation of the highly viscous fibrin in the medical field, in providing tissue sealant, it has become common to provide inline mixing of two or more components—in lieu of batch or tank mixing of the components—to form a tissue sealant, just prior to its application on a work surface. Some sealant products that may provide suitable mixtures include FLOSEAL, COSEAL, TISSEEL and ARTISS sealants from Baxter Healthcare Corporation, OMINEX sealants from Johnson & Johnson and BIOGLUE sealants from Cryolife, Inc. Such sealant may be applied by a dispenser that ejects sealant directly onto the tissue or other substrate or working surface. Examples of tissue sealant dispensers are shown in U.S. Pat. Nos. 4,631,055, 4,846,405, 5,116,315, 5,582,596, 5,605,255, 5,665,067, 5,989,215, 6,461,361 and 6,585,696, 6,620,125, 6,802,822, PCT Publication No. WO 96/39212, and US Pat. Appl. Pub. 2009/0038701, all of which are incorporated herein by reference. Further examples of such dispensers also are sold under the Tissomat™ and Duploject™ trademarks, which are marketed by Baxter AG. Typically, in these devices, two individual streams of the components fibrinogen and thrombin are combined and the combined stream is dispensed to the work surface. Combining the streams of fibrinogen and thrombin initiates the reaction that results in the formation of the fibrin sealant. While thorough mixing is important to promote fibrin formation, fouling or clogging of the dispenser tip by the formation of fibrin prior to dispensing can interfere with proper functioning of the dispenser. Such clogging or fouling may result from contact or mixing of the sealant components in a dispenser and maintaining the mixture in the dispenser for an extended period of time prior to ejection of the mixture from the dispensing tip.

In current mixing systems, the quality of mixing of two or more components having different viscosities may vary depending on the flow rate. For example, under certain flow conditions, the components may be dispensed as a less than thoroughly mixed stream. Accordingly, there is a desire to provide a mixing system which is not dependent on the flow rate to achieve sufficient mixing.

Although prior devices have functioned to various degrees in forming and dispensing mixtures, there is a continuing need to provide a mixer and dispensing system that provides reliable and thorough mixing of at least two components (such as, for example, for a tissue sealant) for application to a desired work surface or other use applications in other fields. Such a mixing system could be provided to dispense the mixture just prior to or at least in close proximity to its intended use or application. Preferably, such a mixer and dispensing system would also mix the components and rapidly dispensing the mixture from the system without allowing internal low flow or stagnant zones to form and thereby avoid undue fouling or clogging of the dispenser.

In addition, the medical procedure may require an interruption in the dispensing. Should the interruption be extended, fibrin will form in any mixture that resides in the dispensing tip, which will likely lead to clogging of the tip. Therefore, after such an interruption the dispensing tip should be able to be easily replaced with a new tip to allow the dispensing to resume.

SUMMARY

In order to eliminate at least some of these drawbacks, the invention provides a spray head in which the components to be mixed are kept separated before they arrive at a mixing element in the spray head.

In an embodiment, the invention provides a device for mixing at least two separate streams of components which, when mixed, form a combined fluid stream. The device comprises a conduit with at least two separate passageways defined by passageway walls, each passageway communicating with a separate component stream and arranged to direct the separate component stream in a downstream direction towards exit openings of the passageways in an end face of the conduit, the exit openings each having a predetermined cross-sectional flow area. A separator element is engaged with the end face of the conduit. The separator element has a separate channel communicating with each passageway. A mixing chamber communicates with all of the separator element channels, the mixing chamber being arranged to receive each of the component streams at an upstream end thereof and to permit a mixing of the component streams. An outlet is arranged downstream of the mixing chamber through which the combined fluid stream is dispensed.

In an embodiment, the device includes a mixing element positioned at a downstream end of the mixing chamber, the mixing element being configured to thoroughly mix the component streams into the combined fluid stream.

In an embodiment, the mixing element comprises a three-dimensional lattice defining a plurality of tortuous, interconnecting passages therethrough.

In an embodiment, the device includes a spray nozzle arranged at the outlet to dispense the combined fluid stream.

In an embodiment, the spray nozzle comprises a swirl nozzle.

In an embodiment, the separate channels are defined by internal walls of the separator element to separate the channels from one another and configured such that each separate channel communicates with only one of the passageways.

In an embodiment, the separator element comprises a number of separate channels which is twice the number of passageways.

In an embodiment, each of the separate channels has a cross-sectional area greater than the cross-sectional area of its respective passageway exit opening.

In an embodiment, the separator element and the mixing chamber are provided in a removable spray head separate from the conduit housing the at least two separate passageways, the removable spray head attaching to the passageway conduit via a luer fitting.

In an embodiment, the separator element and mixing chamber are configured to compensate for variations in the dimensions of the luer fitting and engagement between the spray head and passageway conduit.

In an embodiment, the passageway exit openings in the end face are angularly spaced apart from each other at equal angular orientations.

In an embodiment, the mixing chamber element comprises two separate channels for every passageway and internal longitudinal separation walls are provided between each of the separate channels, the internal longitudinal separation walls being arranged at angular positions, relative to one another, which are at angles one half of the angles of the angular orientations of the passageway exits.

In an embodiment, the invention provides a device for mixing at least two separate streams of components, which when mixed, form a combined fluid stream. The device comprises a conduit with at least two separate passageways defined by passageway walls, each passageway communicating with a separate component stream and arranged to direct the separate component stream in a downstream direction towards exit openings of the passageways in an end face of the conduit. The exit openings each having a predetermined cross-sectional flow area. A separator element is engaged with the end face of the conduit. The separator element has a separate channel communicating with each passageway. A single mixing chamber communicates with all of the separate channels. The mixing chamber is arranged to receive each of the component streams at an upstream end thereof and to permit a mixing of the component streams. A mixing element is positioned at a downstream end of the mixing chamber. The mixing element is configured to thoroughly mix the component streams into the combined fluid stream. A spray nozzle is arranged downstream of the mixing element to dispense the combined fluid stream.

In an embodiment, the conduit comprises two separate passageways.

In an embodiment, the separate channels each have a larger cross-sectional flow area than their associated passageway exit opening.

In an embodiment, the separator element is positioned in an upstream end of the mixing chamber. The separator element has internal walls to separate the channels from one another and is arranged such that each channel communicates with only one of the passageways.

In an embodiment, the separator element comprises a number of separate channels which is twice the number of passageways.

In an embodiment, the mixing chamber has a cross-sectional flow area larger than the cross-sectional flow area of each channel of the separator element.

In an embodiment, the mixing chamber has a cross-sectional flow area larger than a combined total cross-sectional flow area of all of the channels of the separator element.

In an embodiment, the mixing element comprises a three-dimensional lattice defining a plurality of tortuous, interconnecting passages therethrough.

In an embodiment, the spray nozzle comprises a swirl nozzle.

In an embodiment, the mixing chamber is formed in a removable conduit separate from the conduit housing the at least two separate passageways, the removable conduit attaching to the passageway conduit via a luer fitting.

In an embodiment, the conduit housing the at least two separate passageways has a cylindrical outer surface shape, the passageway exit openings being spaced apart from each other at equal angular orientations.

In an embodiment, the separator element comprises two separate channels for every passageway and internal longitudinal separation walls are provided between each of the separate channels, the internal longitudinal separation walls being arranged at angular positions, relative to one another, which are at angles one half of the angles of the angular orientations of the passageway exit openings.

In an embodiment, a thickness of the internal longitudinal separation walls is less than one half of a diameter of the passageway exit openings.

In an embodiment, a Y-shaped passage is positioned between the mixing element and the spray nozzle through which the combined fluid stream flows towards the spray nozzle.

In an embodiment, the invention provides a device for mixing two separate streams of components which, when mixed, form a combined fluid stream. The device comprises a conduit having a generally cylindrical external surface with two separate internal passageways, each passageway communicating with a separate component stream and arranged to direct the separate component stream in a downstream direction. The passageways terminate at an end face of the conduit at exit openings which each have a predetermined cross-sectional flow area identical to the other. The exit openings are angularly spaced from each other by 180 degrees. A removable conduit is securable to the passageway conduit via a luer fitting, and has a mixing chamber located therein. A separate separator element is positioned in an upstream end of the mixing chamber and engages the end face of the conduit. The separator element has four internal longitudinal walls angularly spaced from one another by 90 degrees to separate four separate channels from one another. A thickness of the longitudinal walls is less than one half of a diameter of the exit openings of the passageways and the separate channels each have a larger cross-sectional flow area than the passageway exit openings. The longitudinal walls direct the component streams in a downstream direction. The separate channels each communicate at downstream ends thereof with the mixing chamber to permit a mixing of the component streams in the mixing chamber. A mixing element is positioned at a downstream end of the mixing chamber. The mixing element is configured to thoroughly mix the component streams into the combined fluid stream. A spray nozzle is arranged downstream of the mixing element to dispense the combined fluid stream.

BRIEF DESCRIPTION OF THE DRAWINGS

The invention will be better understood on reading the following description, given solely as an example, and by referring to the appended drawings in which:

DETAILED DESCRIPTION

Figure 1:
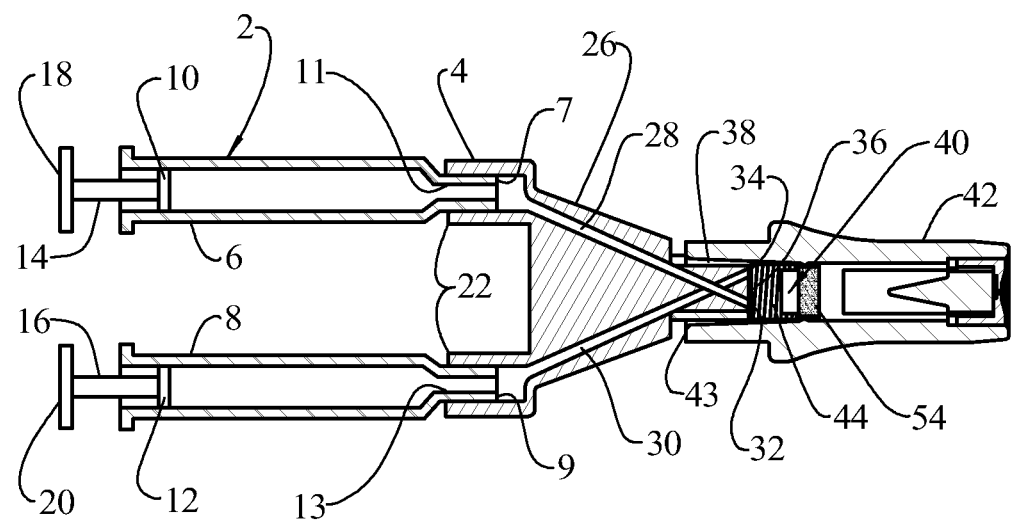
FIG. 1 is a partial cross-sectional view of one embodiment of a tissue sealant dispenser set forth in the present disclosure.

In accordance with one embodiment of the present invention, FIG. 1 illustrates a dispenser, generally indicated at 2 and having a tip structure 4, for mixing at least two separate streams of components into a combined fluid stream, such as a sealant, or tissue sealant or other combined fluid stream. Although the dispensers, systems and methods are generally illustrated and described in the context of a tissue sealant dispenser, it is understood that the present invention is not limited to such a dispenser or to the mixing of tissue sealant components, and that the present invention has applications in a variety of settings where mixing of component fluid streams is desired As shown in FIG. 1, dispenser 2 includes at least two fluid component sources, illustrated in the form of hollow cylinders or barrels 6 and 8, although other source containers from which fluid components are provided may be used. In the embodiment of FIG. 1, each barrel 6, 8 has a generally cylindrical interior or bore in which one of the fluid components such as fibrinogen or thrombin for forming fibrin tissue sealant is stored. The distal end 7, 9, respectively, of each barrel has an outlet port 11, 13, respectively, for communicating with the dispensing tip structure, generally at 4.

In FIG. 1, the bore of each barrel 6, 8 preferably slidably receives a piston or plunger 10, 12, respectively, for ejecting the sealant component from the respective bore. A plunger or pusher 14, 16 is associated with each piston and extends proximally from each respective bore. A thumb-rest 18, 20 is preferably associated with each plunger 14, 16 and may be actuated or pushed manually or automatically to eject the component. The thumb-rests 18, 20 may be actuated either independently or simultaneously, such as by a common actuator or yoke that couples the plungers together for simultaneous movement.

As shown in FIG. 1, the illustrated tip assembly or structure is a multi-part assembly and includes a flow director or Y-piece 26. The Y-piece 26 has a proximal end 22 and a distal end 24 and comprises walls that define respective first and second passageways 28 and 30. Each passageway 28, 30 communicates with a respective bore of the barrels 6, 8 to allow the respective component to exit the distal end 24 in a downstream direction. As shown in FIG. 1, the inlet to each passageway 28 and 30 is suitable for attachment to one of the outlets from barrels to 6, 8 such as, for example, by a luer fitting or other attachments as will be apparent to persons of skill in the relevant field.

Although manually actuated plungers are illustrated for dispensing the fluid components, other types of devices may be used in connection with the present invention including manually or electrically actuated dispensers. Further, as noted above, it is contemplated that the present invention is not limited to dispensers for sealant and may be used to combine two or more components for other combined fluid streams for other applications within or outside of the medical field.

In FIG. 1, each of the first and second passageways 28, 30 communicates with one of the components as a separate fluid stream and directs the separate fluid streams out of exit openings 32, 34 located in an end face 36 of the Y-piece 26. The exit openings 32, 34 of each passageway 28, 30 have a predefined cross-sectional area through which each component flows. The cross-sectional areas preferably are sized to correspond to a ratio of the amount of the two components that are to be mixed. In the illustrated embodiment, the cross-sectional areas are identical, so the components will be mixed in a 1:1 ratio, however, other ratios may be selected.

The Y-piece 26 is a conduit in which the passageways 28, 30 are located, and near the end face 36, the Y-piece has a generally cylindrical shaped outer surface 38 which may be slightly tapered to provide a luer tip fitting. As shown in FIG. 1, the first and second passageways 28, 30 extend linearly along their length for ease of manufacturing. The passageways 28, 30 extend at an angle relative to one another such that the directions of the fluid flow out of the exit openings 32, 34 at the end face 36 are not parallel to one another or parallel to the axis of the Y-piece as the fluid component streams are directed into a mixing space 40. In the embodiment illustrated, the mixing space 40 comprises a cylindrical open space, although other shapes may be provided as well.

Figure 2:
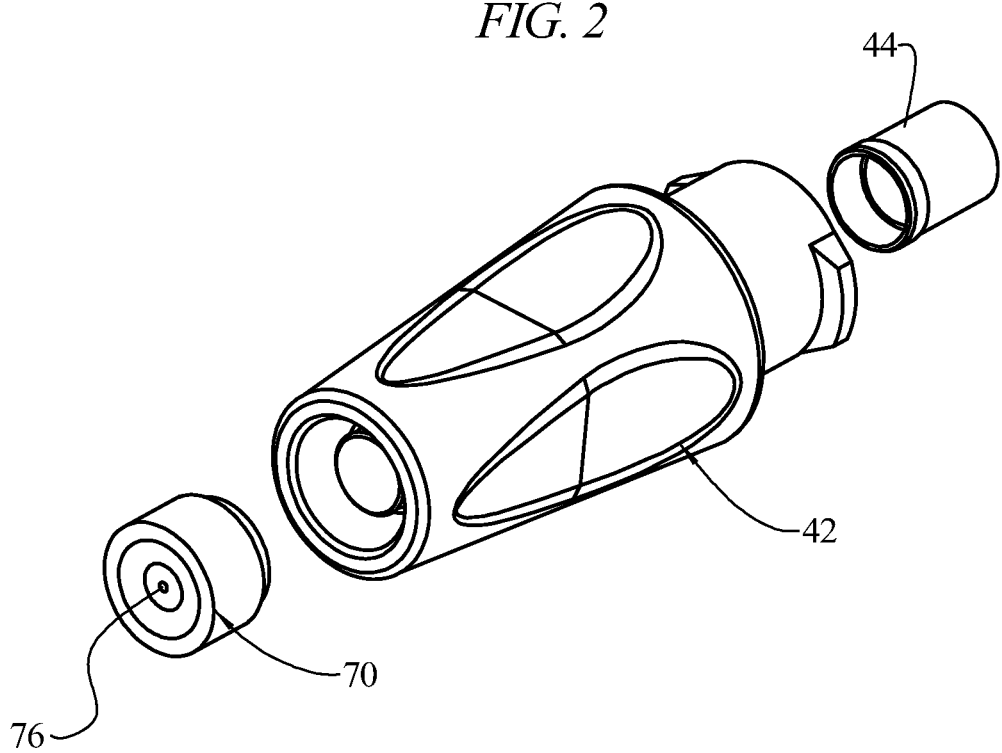
FIG. 2 is a perspective exploded view of a first embodiment of a spray head assembly portion of the dispenser of FIG. 1.
Figure 3:
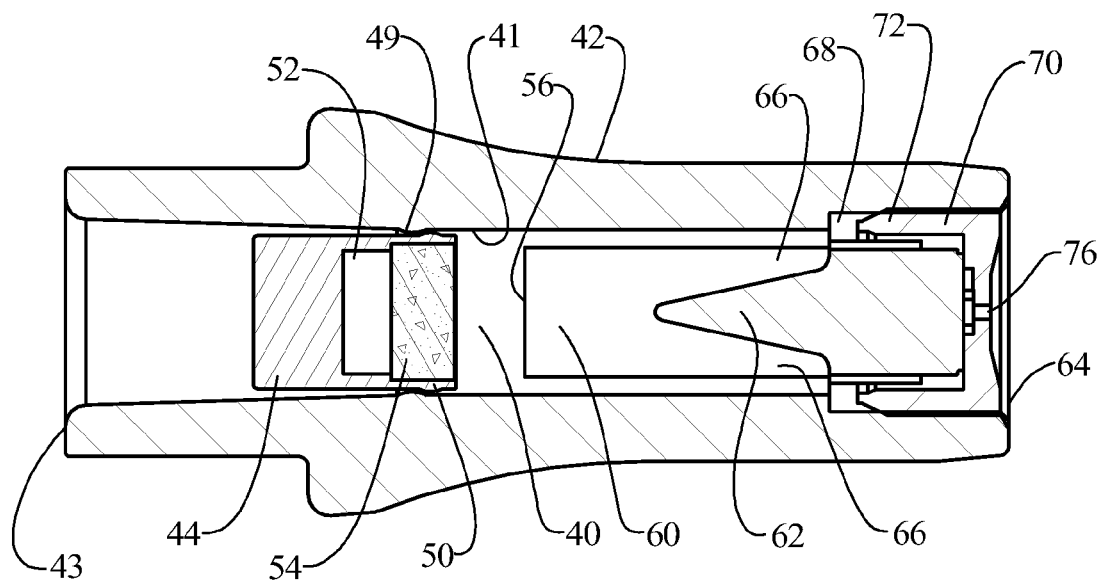
FIG. 3 is a longitudinal cross-sectional view of the spray head assembly of FIG. 2.

The mixing space 40 may be located in an interior passage 41 of a separate spray head body 42, as shown in FIGS. 1, 2 and 3. As illustrated, the separate spray head body 42 acts as a conduit and includes an inlet end 43 which can removably attach to the cylindrical outer surface 38 of the Y-piece 26, such as, for example, by a luer fitting or other attachments as will be apparent to persons of skill in the relevant field. The spray head body 42 includes an exterior surface shaped to provide manual gripping surface areas to facilitate twisting of the spray head body onto the Y-piece 26.

Figure 4:
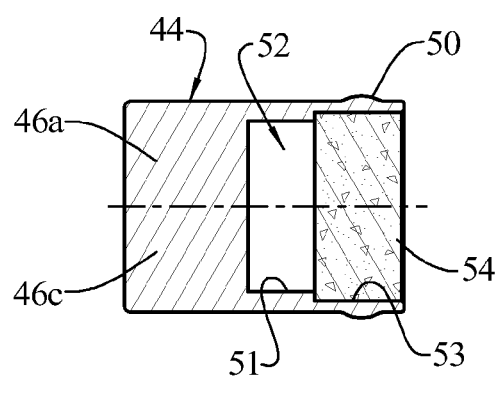
FIG. 4 is a cross sectional view of a separator element of the spray head assembly of FIG. 2.
Figure 5:
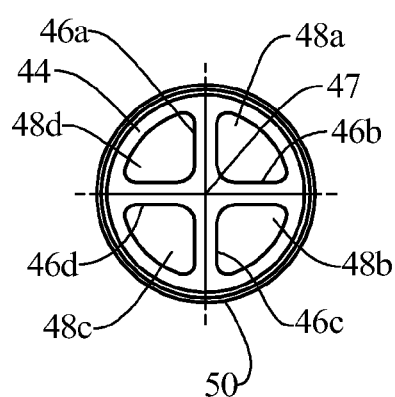
FIG. 5 is an end view of the separator element of FIG. 4.
Figure 6:
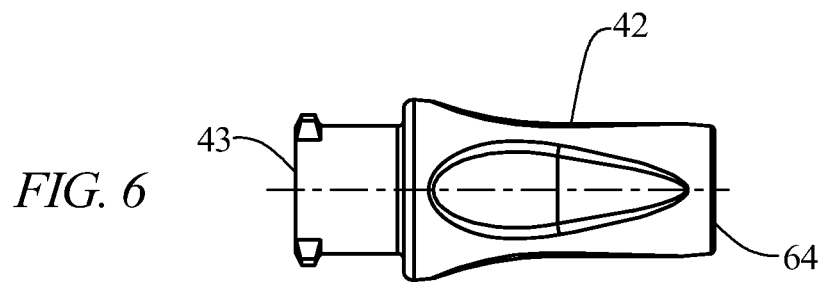
FIG. 6 is a side elevational view of an embodiment of the spray head body of FIG. 2.'

Located in the mixing space 40 is a separator element 44 which, in the illustrated embodiment shown in detail in FIGS. 4 and 5, is a hollow cylindrical member having four longitudinally extending interior walls 46a, 46b, 46c, 46d that are arranged at an angular spacing of 90 degrees from adjacent walls. These four walls 46a, 46b, 46c, 46d extend only a portion of the longitudinal length of the separator element in the embodiment shown in FIG. 4. In this arrangement, the four walls 46a, 46b, 46c, 46d meet at a radial center 47 of the separator element 44. The four walls 46a, 46b, 46c, 46d divide the interior of the separator element 44 into four separate longitudinal channels 48a, 48b, 48c, 48d. The longitudinal channels 48a, 48b, 48c, 48d redirect the angled fluid flow coming from the passageways 30, 32 into an axial direction, and also allow for some lateral expansion of the fluid flow streams. The interior walls 46a, 46b, 46c, 46d each have a thickness that is less than one half of the diameter of the passageway exit openings 32, 34 (shown also in FIG. 11). In a preferred embodiment, the separator element 44 is press fit within the interior passage 41 of the spray head body 42 and in a further embodiment the element 44 is formed of an elastomeric material such that it can be compressed slightly as it is being press-fitted in place, and its resiliency will assist in holding it in place within the spray head body 42.

Figure 10:
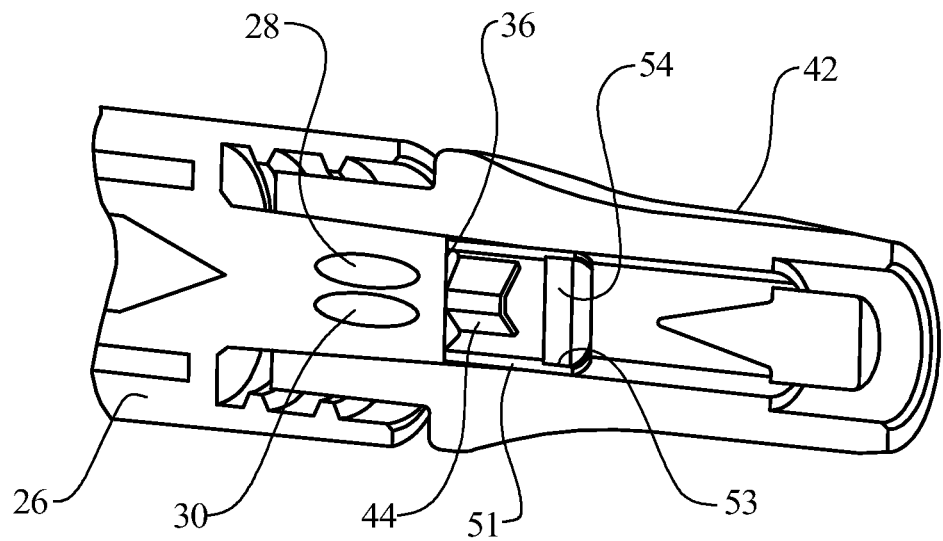
FIG. 10 is a perspective cut-away view of the first embodiment of FIG. 2, with the Y-piece engaged against the separator.

When the spray head body 42 is attached to the Y-piece 26, the separator element 44 is located in abutting relationship to the end face 36 of the Y-piece 26 as shown in FIGS. 1 and 10, such that the exit openings 32, 34 of the passageways 28, 30 will lead directly into the separate channels 48a, 48b, 48c, 48d. A tight engagement between the separator element 44 and the end face 36 may be achieved by using the end face to contactingly press against the separator element 44.

In one embodiment, as illustrated, the interior passage 41 of the spray head body 42 may be provided with a detent 49, such as a raised annular ring, and an exterior surface of the separator element 44 may also be provided with a detent 50. During assembly of the spray head, the separator element 44 is inserted into the interior passage 41 of the spray head body 42, from the inlet end 43, the detent 50 of the separator element will pass the detent 49 of the interior passage, and the flexible and resilient material of the separator element will allow such passage, and will thereafter restore the shape of the separator element such that the separator element will be retained in the spray head body 42 as part of a spray head assembly.

When the spray head body 42 is attached onto the Y-piece 26, the end face 36 of the Y-piece will engage the separator element 44, as shown in FIG. 10, and will move the separator element even further into the interior passage 41 of the spray head body 42. If detents are provided, the engagement of the detent 49 with the separator element 44 and the engagement of the detent 50 with the interior passage 41, along with the resiliency of the separator element will assure that the separator element will remain sealingly engaged with the end face 36 of the Y-piece 26.

An accommodation is provided for Y-pieces 26 having some small variation in the luer tip 38, such as for Y-pieces made by different manufacturers or made in different manufacturing runs, by making the separator element 44 from an elastic and flexible material. That is, the outer surface 28 of the Y-piece 26 and the inlet end 43 of the interior passage 41 are provided with complementary tapers to allow for a snug luer connection between the components. This connection is easily obtained by a twisting movement of the spray head body 42 onto the Y-piece 26. Slight variations in the tapers and/or lengths of the Y-piece 26 at the outer surface (luer tip) 28 up to the end face 36, may result in engagement by the end face with the separator element 44 either earlier or later from one set of components to the next. With the separator element 44 being made of an elastic and flexible material, the walls of the separator element will be able to flex or buckle to effectively shorten the length of the separator element. So, if the end face 36 presses a distal end of the separator element 44 or the mixing element (as described below) against a shoulder (also discussed below) in the interior passage 41 before the luer tip 28 is sealingly engaged with the interior passage of the spray head body 42, the luer tip will be able to continue to move inwardly until the snug connection is made between the Y piece 26 and the spray head body 42.

Further, because the separator element 44 is only loosely (in a longitudinal sense) held in the interior passage 41, the separator element will be able to move longitudinally in the interior passage for some distance before the separator element will be pressed against a fixed stop, such as a shoulder. Therefore, this loose positioning of the separator element 44 within the interior passage 41 will also accommodate some variation of the luer tip.

When the Y-piece 26 is provided with two passageway exit openings 32, 34 angularly spaced apart by 180 degrees, as illustrated, and the separator element 44 is provided with four separate channels 48a, 48b, 48c, 48d, each angularly centered 90 degrees from its neighbors, then the two flow streams from the two passageways 28, 30 will remain separated from each other as the flow streams are re-oriented into an axial direction flow in the separate channels.

Figure 11:
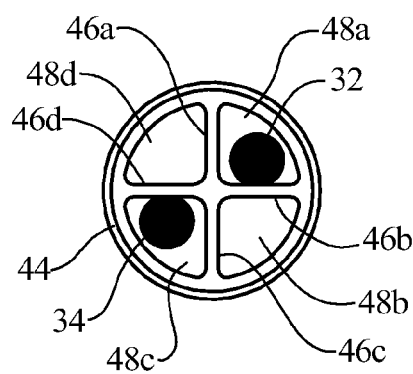
FIG. 11 is an end sectional view at the separator showing the alignment with the passage exit openings in a first random orientation of the separator.

The angular orientation of the separator element 44 within the mixing space 40 is not critical, and the separator element will work effectively in any angular orientation. As illustrated in FIG. 11, in one random orientation of the separator element 44, one of the passageway exit openings 32 aligns nearly completely with one of the separate channels 48a, while the other passageway exit opening 34 aligns with an opposite channel 48c. As the fluid from passageway 28 flows and is directed into an axial direction in one channel, it remains completely isolated from the fluid from passageway 30. It can be seen in FIG. 11 that a cross-sectional area of each separate channel 48a, 48b, 48c, 48d is larger than a cross-sectional area of its associated passageway exit opening 32, 34.

Figure 12:
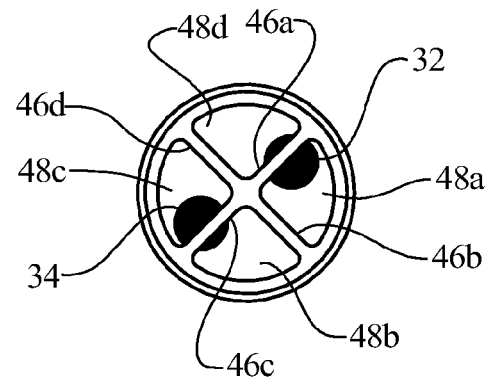
FIG. 12 is an end sectional view at the separator showing the alignment with the passage exit openings in a second random orientation of the separator.

In FIG. 12 there is shown another random angular orientation of the separator element 44 in the mixing space 40. In this orientation, one of the walls 46a intersects the first passageway exit opening 32, such that the first passageway communicates with two adjacent channels 48d and 48a. An opposite wall 46c intersects the second passageway exit opening 34, such that the second passageway communicates with the other two separate channels 48c and 48d. It is seen in FIG. 11 that the thickness of the walls 46a, 46b, 46c, 46d is less than one half of the diameter of the passageway exit openings 32, 34, so as to not severely impede the flow of fluid from the passageways 28, 30 in the event that the walls are positioned directly over a passageway exit opening Even in this orientation, each separate channel 48a, 48b, 48c, 48d communicates with only one passageway 28, 30 so the fluids from the two passageways remain isolated from each other while in the separate channels. In this second orientation, the direction of the fluid flow of the fluids from the passageways 28, 30 are redirected into an axial direction by the walls 46a, 46b, 46c, 46d of the separate channels 48a, 48b, 48c, 48d.

While the embodiment illustrated shows two passageways 28, 30 and four separate channels 48a, 48b, 48c, 48d, other numbers of passageways and channels could be utilized, so long as the exit openings 32, 34 of the passageways are angularly spaced apart at equal angles from each other (at an angle of 360 degrees divided by the number of passageway exit openings) and so long as the separator element 44 is provided with a number of interior longitudinal walls 46a, 46b, 46c, 46d that is twice the number of passageways, and with the longitudinal walls being angularly spaced from each other at half of the angle of the spacing of the exit openings. With such an arrangement, each exit opening will communicate with only one or two adjacent separate channels and the fluid from each passageway will be kept isolated from all other fluids while still in the separator element. In this manner, a separate channel 48a, 48b, 48c, 48d is located at a downstream end of each passageway 28, 30.

In this manner, the user need not be concerned with the relative angular orientation between the spray head body 42 and the Y piece 26 as the two components are being assembled together. The twisting movement of the spray head body 42 onto the Y piece 26 can be made to any extent or degree that the user considers to be necessary to effect the desired tight connection between those two components without any regard or concern with respect to assuring that the exit openings in the Y piece will properly align with appropriate channels in the separator element 44. In any rotational position of the spray head body 42 relative to the Y piece 26, each passageway exit opening will communicate with at least one and no more than two channels and no channel will communicate with more than one passageway exit opening.

The separator element 44, as best seen in FIG. 4, may include an axially extending perimeter wall portion 51 having no interior axially extending walls. This extending perimeter wall portion 51 defines a portion of a mixing chamber 52 communicating at an upstream end with all of the separate channels 48a, 48b, 48c, 48d and in which the fluids from the passageways 28, 30 are free to mix together. In the illustrated embodiment, the cross-sectional area in the mixing chamber 52 is larger than the cross-sectional area of each of the separate channels 48a, 48b, 48c, 48d. Further, in this embodiment, the cross-sectional area of the portion of the mixing chamber 52 within the extending perimeter wall portion 51 is larger than the combined cross-sectional area of all of the separate channels 48a, 48b, 48c, 48d.

The axially extending perimeter wall portion 51 may include a fixture 53, in the form of a recessed space or slightly larger internal diameter, for receiving a mixing element 54 in a press-fit engagement. Although various types of mixing elements 54 may be used, to assist in the thorough mixing of the fluid streams, one effective type of mixing element is described in published US Patent Application 2009/0038701, the description of which is incorporated herein by reference. The mixing element described in that application comprises a three-dimensional lattice defining a plurality of tortuous, interconnecting passages therethrough, the mixer having physical characteristics to sufficiently mix the component streams of the combined fluid stream, the characteristics including a mean flow pore size, thickness and porosity.

By having a fixture 53 for the mixing element 54, a subassembly of the mixing element 54 and the separator element 44 can be assembled prior to the separator element being introduced into the spray head body 42, as shown in FIG. 4. The press fit engagement between the mixing element 54 and the separator element 44, as well as the resiliency of the separator element will retain the mixing element in place.

Figure 13:
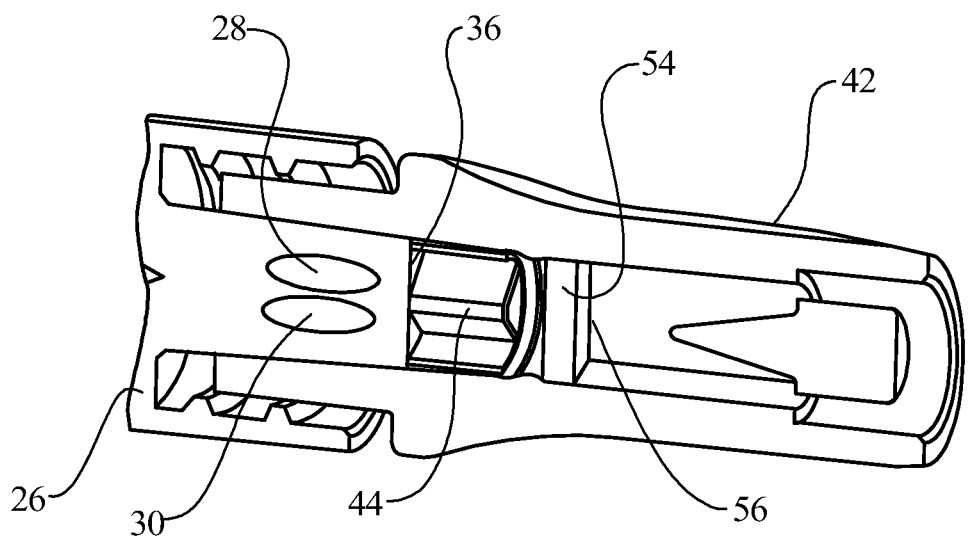
FIG. 13 is a perspective cut-away view of a second embodiment of a spray head according to the invention.

In another embodiment of the invention, as shown in FIG. 13, the mixing element 54 may be located in the mixing space 40 without being held in the separator element 44. In this embodiment, the mixing element 54 will be inserted into the interior passage 41 of the spray head body 42 followed by the insertion of the separator element 44. In an embodiment, the spray head body 42 may be provided with an internal wall or shoulder 56 against which the mixing element 54, if used, may be engaged to prevent an over-insertion of the mixing element.

Figure 7:
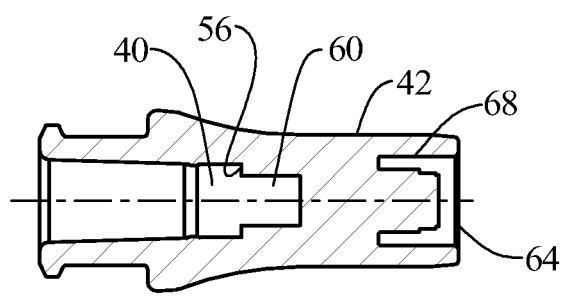
FIG. 7 is a longitudinal cross-sectional view of the spray head body of FIG. 6.
Figure 8:
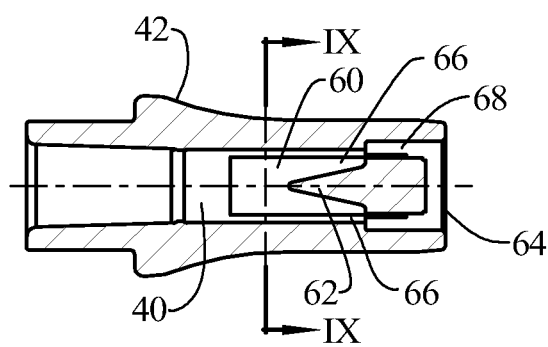
FIG. 8 is a longitudinal cross-sectional view of the spray head body of FIG. 6, rotated 90 degrees relative to FIG. 7.
Figure 9:
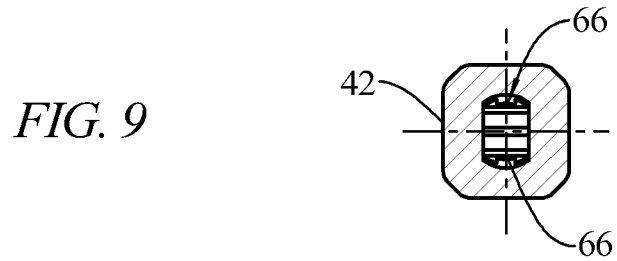
FIG. 9 is a lateral cross-sectional view of the spray head body taken generally along the line IX-IX of FIG. 8.
Figure 14:
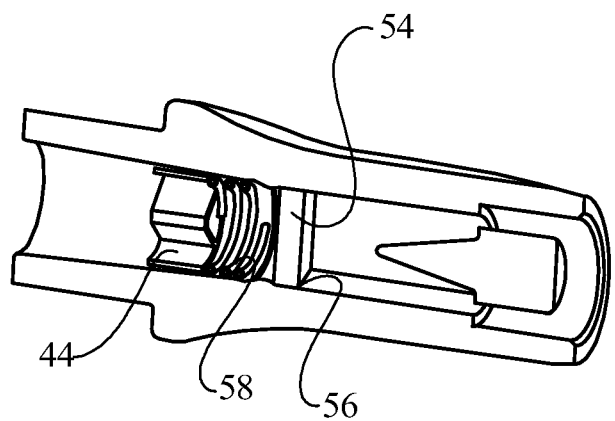
FIG. 14 is a perspective cut-away view of a sliding of the separator into the mixing chamber of the spray head in a third embodiment of a spray head according to the invention.
Figure 15:
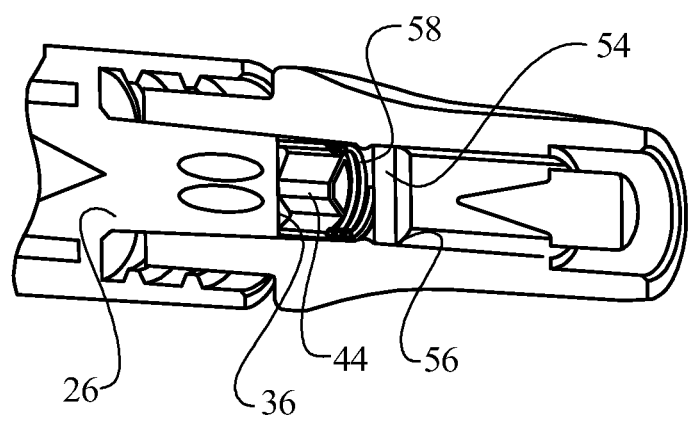
FIG. 15 is a perspective cut-away view of the third embodiment of FIG. 14.

In yet another embodiment, as shown in FIGS. 14 and 15, a spring 58 may be provided between the mixing element 54 and the separator element 44. In FIG. 7, the separator element 44 is shown being inserted into the mixing space 40. In FIG. 14, the separator element 44 is pressed against the spring 58 by the end face 36 of the Y-piece 26. The spring 58 engages against the mixing element 54 which is pressed against the shoulder 56 in the mixing space 40.

Following downstream of the internal wall or shoulder 56 (if present) is an unobstructed space 60 for further mixing of the combined fluid stream. Still further downstream is an integrally formed wedge shaped element 62 which serves to divide the combined fluid stream into two flows which are directed towards an outlet end 64 of the spray head body 42. As soon as the two fluid streams begin to mix together in the mixing chamber 52 after leaving the separate channels 48a, 48b, 48c, 48d, the fluid components begin reacting with one another. In the case of fibrinogen and thrombin, fibrin begins to develop. If the combined flow is allowed to come to a rest or slow significantly, the fibrin will quickly cause the dispenser to become clogged, preventing further dispensing of the combined fluid stream. Therefore, the wedge shaped element 62 is provided downstream of the mixing space 40 to reduce the cross sectional flow area for the combined fluid which results in increasing the stream velocity. Also, the wedge shaped element 62 is shaped to prevent any sharp edges, pockets or corners in the combined stream flow path which would result in dead zones of low flow rate or stagnant fluid thereby allowing clogging formations of fibrin to form.

The wedge shaped element 62 defines two separate passages 66 for the combined flow stream which lead to an annular space 68 near the outlet end 64 of the spray head body 42.

Figure 16:
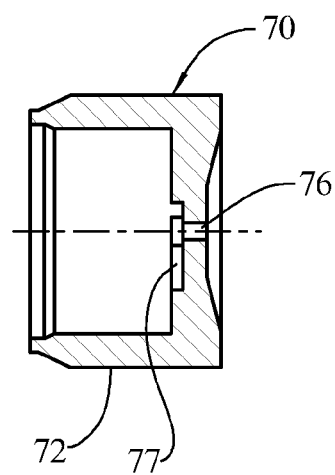
FIG. 16 is a side sectional view of the spray nozzle of the spray head assembly of FIG. 2.
Figure 17:
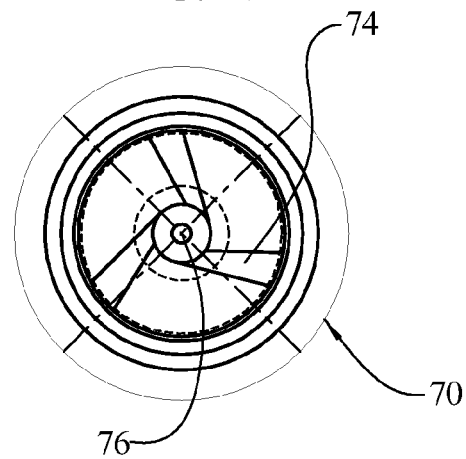
FIG. 17 is an end view of the spray nozzle viewed from the left side of FIG. 16.

Positioned at the outlet end 64 of the spray head body 42 may be a spray nozzle 70, such as a swirl nozzle, as is known, or other mass breakup unit, to cause the departing fluid to be dispersed in the form of a spray of small droplets. The spray nozzle 70, if used, provides for still further mixing of the fluid being dispensed. The spray nozzle 70 may be press fit into the outlet end 64 of the spray head body 42 (see FIG. 3) by means of an annular body 72 (see FIGS. 16 and 17) which is received in the annular space 68 of the spray head body 42. A plurality of flow channels 74 lead to a small outlet orifice 76 where the spray of the combined fluid stream is dispensed. The flow channels 74 may extend tangentially towards the orifice 76 to give the departing spray a spin.

The process of assembling the spray head body assembly in one embodiment includes the step of first preparing a subassembly of the separator element 44 and the mixing element 54 by press fitting the mixing element into the fixture 53 of the separator element. This subassembly can then be introduced into the inlet end 43 of the interior passage 41 of the spray head body 42. If the spray head body 42 and/or the separator element 44 include a detent 49, 50, the subassembly is introduced until the detent is engaged so that the subassembly will be held in place in the spray head body. In embodiments where no detent is provided, the subassembly can be introduced into the interior passage 41 for some distance and the separator element 44 will be held in position merely through the engagement of the elastic outer wall of the separator element with the wall of the interior passage.

In another embodiment where there is no subassembly, the mixing element 54 may be inserted, by itself into the interior passage 41, followed by the insertion of the separator element 44. The presence of the separator element 44 will prevent the mixing element 54 from dislodging from the interior passage 41. The separator element 44 may be held in place in any of the manners described above.

The spray nozzle 70 can also be press fit into the outlet end 64 of the spray head body 42 and will be held in place strictly through a frictional engagement.

The four components of the separator element 44, the mixing element 54, the spray nozzle 70 and the spray head body 42 comprise the spray head body assembly which may be assembled in accordance with the steps described above.

The spray head body assembly can be used in conjunction with the dispenser 2 by the steps of inserting the luer tip 28 of the Y piece 26 into the inlet end 43 of the interior passage 41 of the spray head body 42 (as a part of the spray head body assembly) and twisting the spray head body relative to the Y piece as the insertion occurs. The luer connection between the components will effect a snug and sealed connection between the Y piece 26 and the spray head body 42, and will engage the end face 36 of the Y piece with the separator element 44 so that the passageway exit openings will communicate with only one or two channels, and so that each channel will communicate with no more than one passageway exit opening as described above.

Once the luer connection is made between the Y piece 26 and the spray head body 42, dispensing of the fluid components can commence. A steady and continuous movement of the plungers 10, 12 by a doctor or other medical personnel will result in the separate fluids moving through their dedicated angled passageways 28, 30 in the Y piece 26. As the separate fluids exit from the Y piece 26 they will be redirected by the channels 48*a*, 48*b*, 48*c*, 48*d* in the separator element 44 into an axial direction while at the same time being maintained separate from one another. The separate fluids will exit the channels 48*a*, 48*b*, 48*c*, 48*d* and will be able to begin mixing in the mixing chamber 52, with more complete mixing occurring in the mixing element 54.

As the mixed components exit the mixing element 54, the combined fluid stream will be split into separate streams by the wedge shaped element 62 where the streams will flow through a smaller cross section passage 66 with greater velocity via a smooth transition, and into the annular space 68 in the spray head body 42. From the annular space 68, the combined stream will flow via one of the channels 74 in the spray nozzle 70 to the exit orifice 76 where the combined stream will be broken into small droplets as it is dispensed.

If the plungers 10, 12 are moved continuously, and with sufficient speed, the spray stream will be continuously ejected from the spray nozzle 70, which will prevent clogging of the combined stream in the spray head body 42, such as due to the formation of fibrin. Even brief stoppages of the movement of the plungers 10 12 will generally not cause a clogging of the spray head body 42. However, in some procedures it is necessary to stop the dispensing for some period of time before resuming the dispensing, such as for more than 10 or 20 seconds. In those situations, it may be that the spray head body 42 will become clogged to the extent that fluid can no longer be dispensed from the spray nozzle 70 to a sufficient degree, if at all.

In the case of clogging, the spray head body assembly can be easily and quickly removed and replaced by medical personnel simply by twisting the spray head body 42 relative to the Y piece 26 while pulling the spray head body away from the Y piece to disengage the luer connection. A fresh spray head body assembly can then be assembled onto the Y piece 26 in the manner described above by inserting the luer connection 28 of the Y piece 26 into the inlet 43 of the interior passage 41 of the spray head body 42 and twisting the spray head body relative to the Y piece. By following these steps, the medical personnel can continue to dispense the fluids from the dispenser 2 with a resumption of moving the plungers 10, 12 as described above.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

The invention claimed is:

1. A device for mixing at least two separate streams of components which, when mixed, form a combined fluid stream, the device comprising:

- a conduit with at least two separate passageways, each passageway communicating with a separate component stream and arranged to direct the separate component stream in a downstream direction toward exit openings of the passageways in an end face of the conduit, the exit openings each having a predetermined cross-sectional flow area,
- a separator element engaged with the end face of the conduit, the separator element having at least one separate channel communicating exclusively with each passageway,
- a mixing chamber communicating with all of the separate channels, the mixing chamber being arranged to receive each of the component streams at an upstream end thereof and to permit a mixing of the component streams, and
- an outlet positioned downstream of the mixing chamber through which the combined fluid stream is dispensed.

2. The device according to claim 1 including a mixing element positioned at a downstream end of the mixing chamber, the mixing element being configured to thoroughly mix the component streams into the combined fluid stream.

3. The device according to claim 2, wherein the mixing element comprises a three-dimensional lattice defining a plurality of tortuous, interconnecting passages therethrough.

4. The device according to claim 1 including a spray nozzle positioned at the outlet to dispense the combined fluid stream.

5. The device according to claim 4, wherein the spray nozzle comprises a swirl nozzle.

6. The device according to claim 1, wherein the separator element comprises a number of separate channels which is twice the number of passageways.

7. A device for mixing at least two separate streams of components which, when mixed, form a combined fluid stream, the device comprising:

- a conduit with at least two separate passageways, each passageway communicating with a separate component stream and arranged to direct the separate component stream in a downstream direction toward exit openings of the passageways in an end face of the conduit, the exit openings each having a predetermined cross-sectional flow area,
- a separator element engaged with the end face of the conduit, the separator element having a separate channel communicating with each passageway,
- a mixing chamber communicating with all of the separate channels, the mixing chamber being arranged to receive each of the component streams at an upstream end thereof and to permit a mixing of the component streams, and
- an outlet positioned downstream of the mixing chamber through which the combined fluid stream is dispensed
- wherein the separate channels are defined by internal walls of the separator element to separate the channels from one another and configured such that each separate channel communicates with only one of the passageways.

8. The device according to claim 7, wherein the separator element comprises a number of separate channels which is twice the number of passageways.

9. The device according to claim 1, wherein the mixing chamber has a cross-sectional flow area larger than the cross-sectional flow area of each separate channel.

10. The device according to claim 1, wherein the mixing chamber has a cross-sectional flow area larger than a combined total cross-sectional flow area of all of the separate channels.

11. The device according to claim 1, wherein the separator element and the mixing chamber are provided in a removable spray head separate from the conduit housing the at least two separate passageways, the removable spray head attaching to the passageway conduit via a luer fitting.

12. The device according to claim 1, wherein the passageway exit openings in the end face are angularly spaced apart from each other at equal angular orientations.

13. A device for mixing at least two separate streams of components which, when mixed, form a combined fluid stream, the device comprising:

a conduit with at least two separate passageways, each passageway communicating with a separate component stream and arranged to direct the separate component stream in a downstream direction toward exit openings of the passageways in an end face of the conduit, the exit openings each having a predetermined cross-sectional flow area, a separator element engaged with the end face of the conduit, the separator element having a separate channel communicating with each passageway, a mixing chamber communicating with all of the separate channels, the mixing chamber being arranged to receive each of the component streams at an upstream end thereof and to permit a mixing of the component streams, and an outlet positioned downstream of the mixing chamber through which the combined fluid stream is dispensed, wherein the passageway exit openings in the end face are angularly spaced apart from each other at equal angular orientation, wherein the separator element comprises two separate channels for every passageway and internal longitudinal separation walls are provided between each of the separate channels, the internal longitudinal separation walls being arranged at angular positions, relative to one another, which are at angles one half of the angles of the angular orientations of the passageway exits.

* * * * *